US00PP19596P2

(12) United States Plant Patent
Zaiger et al.

(10) Patent No.: US PP19,596 P2
(45) Date of Patent: Dec. 23, 2008

(54) **INTERSPECIFIC *PRUNUS* TREE NAMED 'HONEY PUNCH'**

(50) Latin Name: *Prunus*
Varietal Denomination: Honey Punch

(76) Inventors: Gary Neil Zaiger, 1207 Grimes Ave., Modesto, CA (US) 95358; Leith Marie Gardner, 4005 California Ave., Modesto, CA (US) 95358; Grant Gene Zaiger, 1907 Elm Ave., Modesto, CA (US) 95358

( * ) Notice: Subject to any disclaimer, the term of this patent is extended or adjusted under 35 U.S.C. 154(b) by 0 days.

(21) Appl. No.: 12/001,979

(22) Filed: Dec. 14, 2007

(51) Int. Cl.
*A01H 5/00* (2006.01)

(52) U.S. Cl. ..... Plt./180

(58) Field of Classification Search ..... Plt./180
See application file for complete search history.

*Primary Examiner*—Kent L Bell

(57) ABSTRACT

A new and distinct variety of interspecific tree. The following features of the tree and its fruit are characterized with the tree budded on 'Nemagaurd' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular bearer of medium to large size fruit.
2. Fruit with attractive red flesh and skin color.
3. Fruit with firm flesh, good handling and storage quality.
4. The tree with a vigorous, upright growth habit.
5. Fruit with a good balance between acid and sugar with an average Brix of 18.8°.

1 Drawing Sheet

Botanical classification: *Prunus* species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES:

Among the existing varieties of plums, apricots and interspecific trees, which are known to us, and mentioned herein, 'Friar' Plum (non-patented), 'Red Beaut' Plum (U.S. Plant Pat. No. 2,539), 'Autumn Giant' Plum (U.S. Plant Pat. No. 5,624), 'Splash' Interspecific (U.S. Plant Pat. No. 14,583), 'Modesto' Apricot (U.S. Plant Pat. No. 2,543), proprietary apricot '386LD394', proprietary plumcot '4G1180' and the plum seedling Q22594A.

ORIGIN OF THE VARIETY:

The new distinct interspecific tree, was originated by us from crosses of the following species, *Prunus salicina* and *Prunus armeniaca* in our experimental orchard located near Modesto, Calif. We crossed a selected seedling of a plum selection received by us from the quarantine station with the identification number 'Q22594A' (see attached quarantine sheet for name and address of quarantine station), with our proprietary interspecific tree, identification number '20Z288'. The pollen parent (20Z288) originated as a first generation cross from our proprietary selections with field identification numbers '326LC131' and '391LD449'. The seed parent (326LC131) originated from the cross of the following varieties; 'Friar' Plum (non-patented), 'Autumn Giant' Plum (U.S. Plant Pat. No. 5,624) and 'Splash' Interspecific (U.S. Plant Pat. No. 4,583). The pollen parent (391LD449) originated from the cross of these varieties; 'Modesto' Apricot (U.S. Plant Pat. No. 2,543) our proprietary plumcot '4G1180' and the proprietary apricot '386LD394'. A large number of these first generation seedlings were grown and budded to established trees of 'Nemagaurd' Rootstock (non-patented) to enhance early production of fruit. Under close and careful observation the present variety exhibited desirable fruit and tree characteristics and was selected in 2003 for additional asexual propagation and commercialization.

ASEXUAL REPRODUCTION OF THE VARIETY:

Additional asexual reproduction of the new and distinct variety of interspecific tree was by budding to 'Nemagaurd' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY:

The present new interspecific tree [Plum]×[((Plum×Plumcot)×Plumcot)×((Apricot×Plumcot)×Apricot)] is of large size, vigorous, upright growth and a productive and regular bearer of medium size, red flesh, clingstone fruit with an attractive red skin color. The fruit is further characterized by having firm flesh, a good balance between acid and sugar, very good flavor and eating quality, with good handling and storage quality. In comparison to its proprietary interspecific pollen parent (20Z288), the new variety is heavier in fruit production, produces larger size fruit, has red flesh compared to yellow and is approximately 30 days later in maturity. In comparison to its seed parent (Q22594A) the fruit of the new variety matures approximately 40 days later.

PHOTOGRAPH OF THE VARIETY:

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY:

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large. Pruned to 3 to 3.5 meters in height and width for economical harvesting of fruit, varies with different cultural practices.

*Vigor.*—Vigorous, tree growth of approximately 1.5 to 2 meters in height the first growing season, varies with soil type and fertility, climatic conditions and cultural practices.

*form.*—Upright, usually pruned to vase shape.

*Branching habit.*—Upright, crotch angle approximately 30°, increases with heavy crop load.

*Productivity.*—Productive, thinning and spacing of fruit necessary for preferred market size.

*Bearer.*—Regular, adequate fruit set 4 consecutive years, no alternate bearing observed.

*Fertility.*—Self sterile, pollinator required.

*Density.*—Medium dense, usually pruned to vase shape to allow more sunlight into center of tree to enhance fruit color and health of fruit spurs.

*Hardiness.*—Hardy in all stone fruit growing areas of California. Tree grown in USDA Hardiness Zone 9. Winter chilling requirement approximately 850 hours at or below 45° F.

Trunk:

*Size.*—Medium. Average circumference 40.6 cm at 20.3 cm above ground on a 6 year old tree.

*Stocky.*—Medium stocky.

*Texture.*—Medium shaggy, becomes rougher with age.

*Color.*—Varies from 7.5YR 2/2 to 10YR 4/2.

Branches:

*Size.*—Medium. Average circumference 14.2 cm at 1 meter above ground. Crotch angle approximately 30°, increases with heavy fruit production.

*Surface texture.*—New growth relatively smooth. Mature growth medium rough, roughness increases with age of growth.

*Lenticels.*—Size — large. Average length 4.0 mm. Average width 1.9 mm. Average number 24 in a 25.8 sq cm section. Color varies from 7.5YR 5/8 to 7.5YR 5/10.

*Color.*—New growth varies from 5GY 5/4 to 5GY 4/4. Mature growth varies from 7.5YR 3/2 to 10YR 3/4, varies with age of growth.

Leaves:

*Size.*—Large. Average length 98.9 mm. Average width 45.0 mm.

*Form.*—Oblanceolate.

*Apex.*—Acuminate.

*Base.*—Cuneate.

*Margin.*—Serrulate.

*Thickness.*—Medium.

*Surface texture.*—Upper surface relatively smooth, slight indentations over midrib and leaf veins, glabrous. Lower surface relatively smooth, except for small ridges created by midrib and pinnate venation, glabrous.

*Petiole.*—Medium. Average length 16.7 mm. Average width 1.8 mm. Longitudinally grooved. Surface — glabrous. Color varies from 2.5GY 7/6 to 2.5GY 6/6.

*Glands.*—Type — globose. Size — small to medium. Average length 0.9 mm. Average diameter 0.5 mm. Number — average number 2, varies from 1 to 3. Located primarily on base of leaf blade and upper portion of petiole. Color varies from 2.5GY 6/6 to 2.5GY 5/6.

*Color.*—Upper surface 5GY 2/2 to 7.5GY 3/2. Lower surface varies from 5GY 4/2 to 5GY 3/2. Midvein color varies from 2.5GY 7/4 to 2.5GY 5/2.

Flower buds:

*Size.*—Small to medium. Average length 8.3 mm. Average diameter 4.5 mm.

*Hardiness.*—Hardy with respect to California winters.

*Form.*—Conical, becoming elongated before opening.

*Pedicel.*—Size — medium. Average length 10.8 mm. Average width 0.6 mm. Surface — glabrous. Color varies from 2.5GY 7/8 to 2.5GY 6/6.

*Color.*—N 9.5/ (white).

*Number of buds per spur.*—Average number 5, varies from 4 to 8, varies with age of spur.

Flowers:

*Size.*—Small to medium. Average height 9.1 mm. Average diameter 17.1 mm.

*Petals.*—Number 5, alternately arranged to sepals. Size — small to medium. Average length 9.3 mm. Average width 6.5 mm. Form — obovate. Margin — sinuate. Both upper and lower surfaces glabrous. Color N 9.5/ (white).

*Sepals.*—Number 5, alternately arranged to petals. Size — small to medium. Average length 3.2 mm. Average width 2.4 mm. Shape — triangular, apex rounded. Margin — entire. Color — upper surface varies from 2.5GY 6/8 to 5GY 6/6. Lower surface varies from 2.5GY 6/6 to 5GY 7/6. Both upper and lower surfaces glabrous.

*Stamens.*—Average number 34. Average filament length 6.8 mm. Filament color N 9.5/ (white). Anther color varies from 5Y 8/8 to 5Y 8/10.

*Pollen.*—Self sterile, pollinator required. Color varies from 5Y 7/10 to 5Y 7/12.

*Pistil.*—Normally one. Surface — glabrous. Average length 8.3 mm. Position of stigma average of 0.5 mm above anthers. Color varies from 10Y 8/6 to 2.5GY 8/8.

*Fragrance.*—Slight aroma.

*Blooming period.*—Date of First Bloom Feb. 23, 2007. Date of Petal Fall Mar. 3, 2007, varies slightly with climatic conditions.

*Color.*—N 9.5/ (white).

*Number flowers per flower bud.*—Average 2, varies from 1 to 4.

*Pedicel.*—Size — medium. Average length 11.1 mm. Average width 0.6 mm. Color varies from 10Y 7/8 to 2.5GY 6/8. Surface — glabrous.

Fruit:

*Maturity when described.*—Firm ripe.

*Date of first picking.*—Aug. 11, 2007.

*Date of last picking.*—Aug. 18, 2007, varies slightly with climatic conditions.

*Size.*—Medium to large. Average diameter axially 61.8 mm. Average transversely in suture plane 67.3 mm. Average weight 164.7 grams, varies slightly with fertility of the soil, amount of thinning and climatic conditions.

*Form.*—Nearly globose, slightly retuse at apex and base of fruit.

*Suture.*—Nearly smooth, extends from base to apex.

*Ventral surface.*—Nearly smooth.

*Apex.*—Slightly retuse.

*Base.*—Varies from flat to retuse.

*Cavity.*—Rounded to very slightly elongated in suture plane. Average depth 7.1 mm. Average diameter 7.7 mm.

Stem:

*Size.*—Medium to large. Average length 16.8 mm. Average diameter 2.1 mm.

*Color.*—Varies from 2.5GY 6/6 to 10YR 3/6.

Flesh:

*Ripens.*—Evenly.

*Texture.*—Firm, meaty.

*Fibers.*—Few, small, tender.

*Firmness.*—Firm, comparable to 'Flavorosa' Interspecific (U.S. Plant Pat. No. 10,285).

*Aroma.*—Slight.

*Amydgalin.*—Undetected.

*Eating quality.*—Very good.

*Flavor.*—Very good with a good balance between acid and sugar.

*Juice.*—Moderate amount, enhances flavor.

*Brix.*—Average Brix 18.8°, varies slightly with amount of fruit per tree and climatic conditions.

*Color.*—Varies from 5R 3/8 to 5R 9/2. Pit cavity varies from 5R 3/4 to 5R 3/8.

Skin:

*Thickness.*—Medium.

*Surface.*—Smooth to slightly waffled.

*Bloom.*—Moderate amount, complete coverage.

*Tendency to crack.*—Very slight.

*Color.*—Ground color varies from 2.5Y 9/4 to 2.5Y 8.5/4. Top color varies from 5R 2/4 to 5R 2/6.

*Tenacity.*—Tenacious to flesh.

*Astringency.*—Undetected.

Stone:

*Type.*—Clingstone.

*Size.*—Medium. Average length 23.4 mm. Average width 18.4 mm. Average depth 11.0 mm.

*Form.*—Ovoid.

*Base.*—Flat.

*Apex.*—Pointed. Average length 1.4 mm.

*Surface.*—Very slightly pitted throughout, one long narrow groove on each side of suture, extending from base to apex.

*Sides.*—Unequal, one side extending further from suture plane.

*Ridges.*—A very small narrow ridge on each side of suture extending from base toward apex.

*Tendency to split.*—None.

*Color.*—Varies from 7.5YR 6/6 to 7.5YR 5/6 when dry.

Kernel:

*Form.*—Ovoid.

*Viability.*—Viable, complete embryo.

*Size.*—Average length 15.1 mm. Average width 10.1 mm. Average depth 5.2 mm.

*Skin.*—Color — varies from 7.5YR 4/6 to 7.5YR 5/6.

Use: Dessert. Market — local and long distance.

Keeping quality: Good, held firm for 21 days in cold storage at 38° to 42° F. without internal breakdown of flesh or appreciable loss of flavor.

Shipping quality: Good, showed minimal skin scarring or flesh bruising during picking, packing or shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of interspecific tree, substantially as illustrated and described, characterized by its large size, vigorous upright growth, being a productive and regular bearer of attractive fruit with red skin and flesh, having very good flavor and eating quality; the fruit is further characterized by having firm flesh, good handling and storage quality and in comparison to the proprietary interspecific pollen parent (20Z288) the new variety is heavier in fruit production, produces fruit that are larger in size, has red flesh compared to yellow and is approximately 30 days later in maturity.

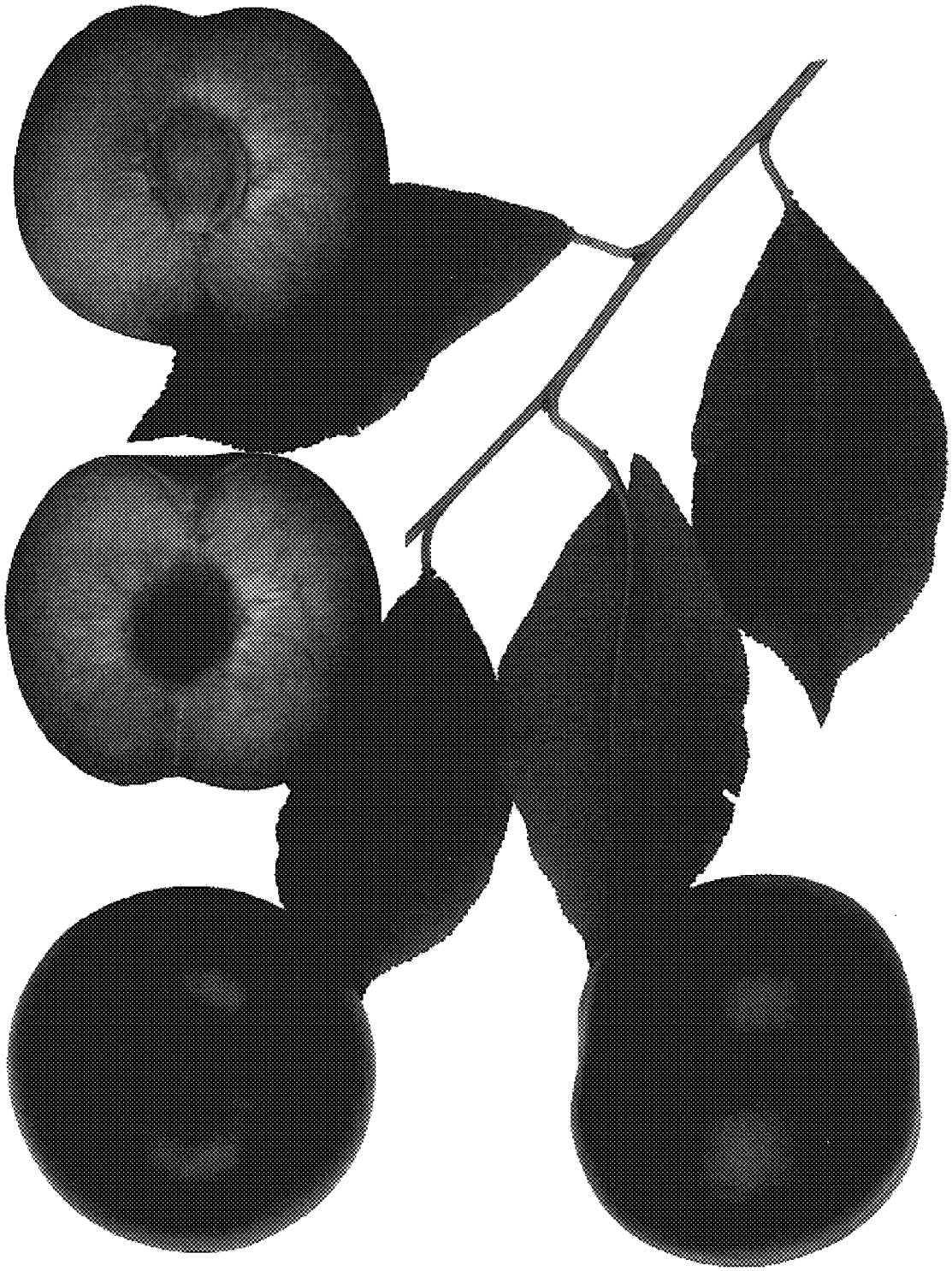

* * * * *